(12) United States Patent
Kilpatrick et al.

(10) Patent No.: US 7,660,454 B2
(45) Date of Patent: Feb. 9, 2010

(54) PROCESS FOR IDENTIFYING FISH SIGNALS

(75) Inventors: Michael Kilpatrick, West Hartford, CT (US); Antti Seppo, Bronx, NY (US); Triantafyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 0 days.

(21) Appl. No.: 11/685,736

(22) Filed: Mar. 13, 2007

(65) Prior Publication Data

US 2007/0243545 A1      Oct. 18, 2007

Related U.S. Application Data

(60) Provisional application No. 60/821,550, filed on Aug. 4, 2006, provisional application No. 60/781,888, filed on Mar. 13, 2006.

(51) Int. Cl.
*G06K 9/00* (2006.01)

(52) U.S. Cl. .................... 382/133; 382/255; 382/284

(58) Field of Classification Search ................ 382/133, 382/134, 173, 255, 284; 356/39, 123
See application file for complete search history.

(56) References Cited

U.S. PATENT DOCUMENTS

2004/0228520 A1* 11/2004 Dresser et al. ............. 382/154
2006/0239534 A1* 10/2006 Sumida et al. ............. 382/133
2008/0212865 A1*  9/2008 Zhu et al. .................. 382/133

OTHER PUBLICATIONS

Blackburn, E.H., "Telomers: No End in Sight", Cell, 1994, pp. 621-623, 77(5).
Moyzis, et al., "A Highly Conserved Repetitive DNA Sequence ...", Proc. Natl. Acad. Sci. USA, 1988, pp. 6622-6626, vol. 85.
Griffith, et al., "Mammalian Telomers End in a Large Duplex Loop", Cell, 1999, pp. 503-514, V.97(4).
Vaziri, et al., "Loss of Telomeric DNA during Aging of Normal and Trisomy 21 Human Lymphocytes", Amer. J. Hum. Gen., 1993, pp. 661-667, vol. 52.
Slagboom, et al., "Genetic Determination of Telomere Size in Humans: a Twin Study of Three Age Groups", Amer. J. Hum. Genet., 1994, pp. 876-882, V. 55(5).
Okuda, et al., "Telomere Attrition of the Human Abdominal Aorta", Atherosclerosis, 2000, pp. 391-398, V. 152(2).
Jeanclos, et al., "Telomere Length Inversely Correlates with Pulse Pressure", Hypertension, 2000, pp. 195-200, vol. 36.

(Continued)

*Primary Examiner*—Andrew W Johns
(74) *Attorney, Agent, or Firm*—Kelly Drye & Warren LLP

(57) ABSTRACT

The invention herein includes a method for combining immuno staining and FISH using covalently bound small molecule tags. Among embodiments included are methods of tagging immuno and FISH probes for treatment of biologic material. Embodiments comprise directing the fluorescently labeled immuno probe(s) to non-chromosomic portions of a biologic sample and directing labeled FISH probe(s) to chromosomic portions of the biologic sample for further identification of subcellular components. Embodiments also comprise the automatic connection of information regarding the sample to image analysis, to subcellular component identification and enumeration in order to affect biomedical decisions.

1 Claim, 1 Drawing Sheet

OTHER PUBLICATIONS

Benetos, et al., "Telomere Length as an Indicator of Biological Aging", Hypertension, 2001, pp. 381-385, vol. 37.

Rufer, et al., "Telomere Length Dynamics in Human Lymphocyte Subpopulations Measured by Flow Cytometry", Nat. Biotechnol, 1998, pp. 743-747, V. 16(8).

Rufer, et al., "Telomere Fluorescence Measurement in Granulocytes and T Lymphocytend Memory T Cells . . . ", J. Exp. Med., 1999, pp. 157-167, V. 190(2).

Son, et al., 2000, "Lineage-Specific Telomere Shortening and Unaltered Capacity for Telomerase Expression . . . ", 2000, J. Immunol., pp. 1191-1196, vol. 165.

Baerrlocher, et al., "Telomere Length Measurement by Florescence in situ Hybridization and Flow Cytometry: Tips and Pitfalls", Cytometry, 2000, pp. 89-99, vol. 47.

Meeker, et al., "Telomere Length Abnormalities Occur Early in the Initiation of Epithelial Carcinogenesis", Clinical Cancer Research, 2004, pp. 3317-3326, vol. 10.

Garcia-Aranda, et al., "Correlations of Telomere Length, Telomerase Activity, and Telomeric-Repeat Binding Factor 1 Expression . . . ", Cancer, 2006, pp. 541-551, vol. 106.

Schroder, et al., "Telomere Length in Breast Cancer Patients Before and After Chemotherapy . . . ", British J. of Cancer, 2001, pp. 1348-1353, vol. 84.

Youngren, et al., "Synchrony in Telomere Length of the Human Fetus", Hum. Genet., 1998, pp. 640-643, V. 102(6).

Okuda, et al., "Telomere Length in the Newborn", Pediatric Research, 2002, pp. 377-381, V. 52(3).

Satillo-Pineiro, et al., "Telomerase Activity and Telomere Length in Primary and Metastatic Tumors . . . ", Pediatric Research, 2004, pp. 231-235, V. 55(2).

Schulze, et al., "Telomere Length Measurements", Proc. First Euroconference on Quantitative Molecular Epiginetics, 2000.

Seuleman, S. "Telomere Length Analysis as a Novel Diagnostic Test for Bladder Cancer", Enq. J. Interdisciplinary Studies for High School Students, 2003, pp. 1-5, V. 1(1).

Taylor, D. Lansing, et al., "The New Technology of Light Microscopy", American Scientist, 1992, pp. 322-335, V. 80(4).

Wu, et al., "Telomere Dysfunction: A Potential Cancer Predisposition Factor", J. Nat. Cancer Ins., 2003, pp. 1211-1218, vol. 95.

Shibata, D., "Biology of Telomere Length Conservation in Breast Cancer", Breast Cancer Research Program, 1995, Cycle I.

Parker, et al., "Telomere Length Indicates Mortality Risk", FuturePundit.com, 2003. http://www.futurepundit.com/archives/000925.html.

Tabori, U., "Younger Age of Cancer Initiation is Associated with Shorter Telomere Length in Li-Fraumeni Syndrome", Cancer Research, 2007, pp. 1415-1418, vol. 67.

Zou, Y., "Telomere Length and Genomic Study as Indicators of Breast Cancer Risk", Texas Univ. Southwestern Medical School at Dallas, 2004, Annual Summary Report No. A290624.

Boultwood, et al., "Telomere Length Shortening in Chronic Myelogenous Leukemia is Associated with Reduced Time to Accelerated Phase", Blood, 2000, pp. 358-361, vol. 96.

Vallejo, et al., "Dynamics of Genetic Information: Fundamental Basis and Cancer", UMR 7147 CNRS/Institut Curie, 2005.

Brummendorf, et al., "Longitudonal Studies of Telomere Length in Feline Blood Cells . . . ", Exp. Hematol., 2002, pp. 1147-1152, vol. 30.

Plohl, et al., "Telomeric Localization of the Vertebrate-Type Hexamer Repeat . . . ", J. Biol. Chem., 2002, pp. 19839-19846, vol. 277.

* cited by examiner

PROCESS FOR IDENTIFYING FISH SIGNALS

CROSS-REFERENCE TO RELATED APPLICATION

This application claims benefit under 35 U.S.C. §119(e) from U.S. Provisional Applications Ser. Nos. 60/821,550 filed on Aug. 4, 2006 and 60/781,888 filed on Mar. 13, 2006.

All references cited in this specification, and their references, are incorporated by reference herein where appropriate for teachings of additional or alternative details, features, and/or technical background.

BACKGROUND OF THE INVENTION

1. Field of the Invention

The present invention includes a method for combining immunostaining and FISH using covalently binding small molecule tags.

2. Description of the Related Art

Many methods are known to aid in the microscopic analysis of samples. For example, without limitation, it is known that certain dyes have an affinity for certain cellular structures. Such dyes may therefore be used to aid in analysis by helping to further elucidate such structures.

Fluorescence microscopy of cells and tissues is well known in the art. Methods have been developed to image fluorescent cells in a microscope and extract information about the spatial distribution and temporal changes occurring in these cells. Some of these methods and their applications are described in an article by Taylor, et al. in American Scientist 80 (1992), p. 322-335. These methods have been designed and optimized for the preparation of a few specimens for higher spatial and temporal resolution imaging measurements of distribution, amount and biochemical environment of the fluorescent reporter molecules in the cells.

Detection of fluorescent signals may be by way of an epifluorescent microscope which uses emitted fluorescent light to form an image (whereas a conventional reflecting microscope uses scattered illumination light to form an image). The excitation light of an epifluorescence microscope is used to excite a fluorescent tag in the sample causing the fluorescent tag to emit fluorescent light. The advantage of an epifluorescence microscope is that the sample may be prepared such that the fluorescent molecules are preferentially attached to the biological structures of interest thereby allowing identification of such biological structures of interest.

The acronym "FISH" references a technique that uses chromophore tags (fluorophone) that emists a secondary signal if illuminated with an light to detect a chromosomal structure. FISH uses fluorescent probes which bind only to those parts of the chromosome with which they show a high degree of sequence similarity. Such tags may be directed to specific chromosomes and specific chromosome regions. The probe has to be long enough to hybridize specifically to its target (and not to similar sequences in the genome), but not too large to impede the hybridization process. Typically, the probe is tagged directly with fluorophores. This can be done in various ways, for example nick translation or PCR using tagged nucleotides. If signal amplification is necessary to exceed the detection threshold of the microscope (which depends on many factors such as probe labelling efficiency, the kind of probe and the fluorescent dye), secondary antibodies or streptavidin are bound to the tag molecules, thus amplifying the signal.

The FISH technique may be used for identifying chromosomal abnormalities and gene mapping. For example, a FISH probe to chromosome 21 permits one to "fish" for cells with trisomy 21, an extra chromosome 21, the cause of Down syndrome. FISH kits comprising multicolor DNA probes are commercially available For example. AneuVysion Multicolor DNA Probe Kit sold by the Vysis division of Abbott Laboratories, is designed for in vitro diagnostic testing for abnormalities of chromosomes 13, 18, 21, X and Y in amniotic fluid samples via fluorescence in situ hybridization (FISH) in metaphase and interphase nuclei. The AneuVysion Assay (CEP 18, X, Y-alpha satellite, LSI 13 and 21) Multicolor Probe Panel uses CEP 18/X/Y probe to detect alpha satellite sequences in the centromere regions of chromosomes 18, X and Y and LSI 13/21 probe to detect the 13q14 region and the 21q22.13 to 21q22.2 region. The combination of colors evidenced is used to determine whether there is normal chromosome numbers or trisomy. In a similar vein, the UroVysion kit by the Vysis division of Abbott Laboratories is designed to detect chromosomal abnormalities associated with the development and progression of bladder cancer by detecting aneuploidy for chromosomes 3, 7, 17, and loss of the 9p21 locus via fluorescence in situ hybridization (FISH) in urine specimens from persons with hematuria suspected of having bladder cancer.

Another process for detecting structures of interest is immunostaining. Immunostaining refers to the laboratory process of detecting biological materials using antibodies. Often these antibodies are labeled with a fluorescent compound which can be viewed by a microscope. Antibodies that detect, for example, a protein of interest in the biological sample are generated by a foreign host species (a polyclonal antibody) or cultured immune cell clones (monoclonal antibodies). After exposure to the foreign protein, the antibodies can be harvested and used as very specific and sensitive detection agents. Antibodies so generated are known as "primary antibodies," as they bind directly to the protein of interest. Certain immunostaining agents can be applied in a single stage, where the primary antibody is directly linked to a colouring agent. In other cases, the primary antibody is targeted by a "secondary" antibody, targeting a species-specific part of the structure of the primary antibody. The later technique may be advantageous in that the signal is amplified, as multiple secondary antibodies will bind to a primary antibody. It also allows for a high variety of primary antibodies— researchers can make their own antibodies and not have to conjugate them to a colouring agent themselves. Finally, it means that a variety of colouring agents can be conjugated to any given species of secondary antibody, and are available in ready supply. This has opened the door to "double-labelling" experiments, where several proteins can be co-localised.

Traditionally the combination of immunostaining techniques with FISH has been challenging. If immunostaining is performed first, subsequent FISH treatment may abolish mostly non-covalent antibody-antigen interaction. Similarly, if FISH is performed first, the subsequent antibody treatment may release the FISH probe because of its low salt concentration. As the immunostaining of certain portions of a biological sample as well as the FISH staining of other areas of the same biological sample may be advantageous, it would be advantageous if a system allowing for combined immunostaining and FISH staining could be developed.

SUMMARY OF THE INVENTION

Embodiments disclosed herein include:

A method comprising in order: (a) treating a biological sample having chromosomal material therein with one or more antibodies having an affinity for at least one non-chromosomal portion of such biological sample the antibody(ies) having an introduced non-detectable reactive conjugate thereon; (b) treating said biological sample with a fluorescently-tagged chromosome probe having a high degree of sequence similarity to one or more portions of said chromosomal material; and (c) treating said biological sample with a detectable tag reactive with said non-detectable reactive conjugate on said antibody(ies) but not with said chromosomal material or non-chromosomal portions of said biological sample. The non-detectable reactive conjugate may be a biontinylated tyramide, and the detectable tag reactive therewith may be streptavidin tagged with a fluorophore.

Alternatively, there is provide a method comprising in order: (a) treating a biological sample having chromosomic material therein with one or more antibodies having an affinity for at least one non-chromosomal portion of such biological sample, the antibody (ies) having introduced a detectable reactive conjugate thereon; (b) treating said biological sample with a fluorescently-tagged chromosome probe having a high degree of sequence similarity to one or more portions of said chromosomic material; and (c) treating said biological sample with a non-detectable or detectable tag reactive with said detectable reactive conjugate on said antibody(ies) but not with said chromosomic material or non-chromosomal portions of said biological sample.

Alternatively, there is provide a method comprising in order: (a) treating a biological sample having chromosomic material therein with one or more antibodies having an affinity for at least one non-chromosomal portion of such biological sample, the antibody (ies) having an introduced a detectable reactive conjugate thereon; (b) treating said biological sample with a fluorescently-tagged chromosome probe having a high degree of sequence similarity to one or more portions of said chromosomic material; and (c) treating said biological sample with a non-detectable or detectable tag reactive with said detectable reactive conjugate on said antibody(ies) but not with said chromosomic material or non-chromosomal portions of said biological sample.

Further provided is a method for fixing biological material to a surface, said method comprising the steps of (a) obtaining a biological sample in an aqueous supernatant and placing a least a portion of said sample on a surface to which part of the sample is to be fixed; (b) removing aliquot volumes of said supernatant replacing the same with a similar volume of alkyl alcohol wherein said removal and replacement occurs a plurality of times so as to gradually fix the part of sample to the surface. The alkyl alcohol may be a $C_1$-$C_{12}$ alcohol, a $C_1$-$C_6$ alcohol, or methanol.

Yet further provided is a method for loading a density centrifugation gradient, said method comprising the steps of: (a) preparing a centrifugation gradient; (b) applying sample to said centrifugation gradient by means of a capillary funnel.

Also disclosed is a method for the simultaneous identification of multiple sub-cellular components, said method comprising the steps of immunostaining a sample of cells with antibodies specific to each of said sub-cellular components to be identified; simultaneously processing said sample of cells with one or more fluorescent in situ hybridization probes comprising distinct fluorophores to discriminate between each of said sub-cellular components to be identified; visualizing and quantitating fluorescent signals produced by said probes in a microscopy system.

Further disclosed is a process for identifying and enumerating fluorescent in situ hybridization ("FISH") signals produced with respect to nuclear components hybridized in situ with fluorescent markers; acquiring 200 using an epi-fluorescence microscope a plurality of images at different focal planes in each fluorescence channel corresponding to the hybridized FISH markers; selecting 300 a best focused image from said plurality of images for each nucleus; acquiring 400 using said epi-fluorescence microscope a plurality of images above and below the focal plane of said best focused image for each nucleus, selecting 500 for each nucleus the one focal plane above and the one focal plane below the focal plane of said best focused image in which the image is best focused, combining 600 said images from the one focal plane above and below said best focused image with said best focused image each nucleus to produce a combined image for said nucleus; analyzing 700 the combined image of each nucleus to separate background pixels from signal pixels, and to determine areas of produced signals corresponding to pre-set size and shape criteria corresponding to a non-artifactual target.

DETAILED DESCRIPTION OF THE INVENTION

Figure 1:
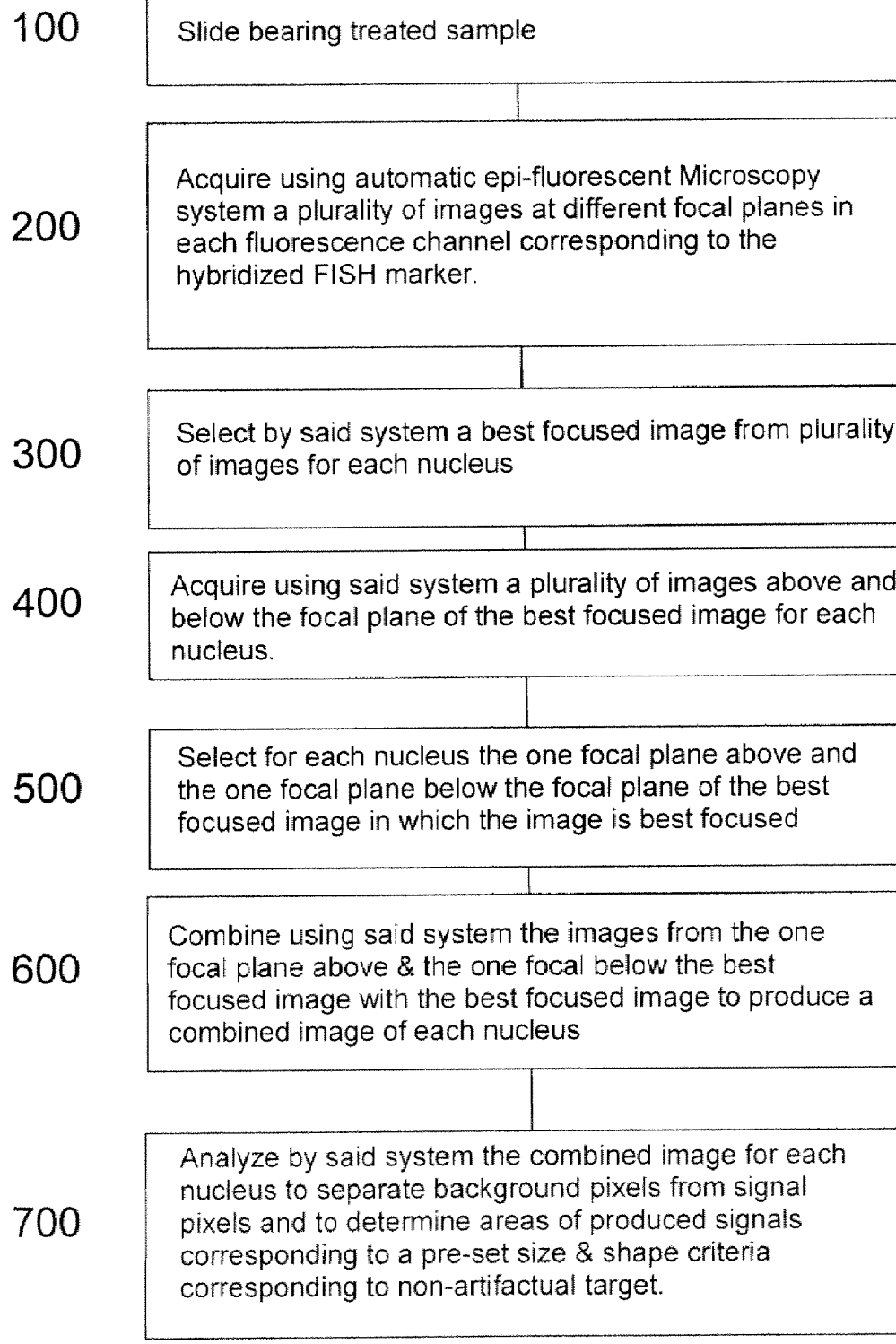
FIG. 1 is a flow chart summarizing the method of one aspect of the invention.

There is disclosed herein a number of techniques for marking subcellular components of a cell to allow for identification of the same, and biomedical decisions to be made based on images of the same.

In one embodiment subcellular component are stained using an immunostaining comprising antibodies specific to each of the sub-cellular components to be identified, and tagging with one or more FISH probes comprising distinct fluorophores that discriminate between each of the sub-cellular components to be identified. The signals produced are quantitated by an automated microscopy system.

In one embodiment, there is disclosed a process of identifying and enumerating fluorescent in situ hybridization ("FISH") signals produced with respect to nuclear components hybridized in situ with fluorescent markers, the process comprising the steps of (a) 200 acquiring using an epi-fluorescence microscope a plurality of images at different focal planes in each fluorescence channel corresponding to the hybridized FISH markers; (b) 300 selecting a best focused image from said plurality of images for each nucleus; (c) 400 acquiring using said epi-fluorescence microscope a plurality of images above and below the focal plane of said best focused image for each nucleus; (d) 500 selecting for each nucleus the one focal plane above and the one focal plane below the focal plane of said best focused image in which the image is best focused; (e) 600 combining said images from the one focal plane above and below said best focused image with said best focused image to produce a combined image for said nucleus, (f) 700 analyzing the combined image for each nucleus to separate background pixels from signal pixels, and to determine areas of produced signals corresponding to a pre-set size and shape criteria corresponding to a non-artifactual target.

In another embodiment there is provided a method for the simultaneous identification of multiple sub-cellular components, the method comprising the steps of (a) immunostaining a sample of cells with antibodies specific to each of the sub-cellular components to be identified; (b) simultaneously process the sample of cells with one or more fluorescent in situ hybridization probes comprising distinct fluorophores to discriminate between each of the subcellular components to be identified; and (c) visualizing and quantitating fluorescent signals produced by the probes in a microscopy system.

The sub-cellular component may be any cell component. For example, the sub-cellular component may be one indicative of developmental age. For example, telomeric length may be determined from signals and used to determine the age of the cell.

Testing may be performed on a host of microscope slides, and such slides may be optionally coded with digitally readable information which describes the sample thereon or the test to performed on the sample.

For example, a microscope slide having a poly-L-lysine coating thereon along at least an area wherein the sample is to be deposited on the slide may be utilized. A poly-L-lysine coating aids in cell, cellular material, and other biological material adhesion to the slide. Application of the biological material to the slide portion coated with poly-L-lysine may be aided by use of a walled chamber with at least a partially opened top and bottom portion, into which the material to be deposited on the slide may be placed. The walled chamber may be connected to a base which is operatively configured for holding a microscope slide which may be coded, and intercalated therewith (e.g. in a tongue and groove configuration). The portion of the microscope slid onto which the sample is placed can be positioned under the wall structure in a manner such that a defined area of coverage is set. The walled chamber may be pinioned at a fixed point to allow the walled chamber to be pivoted up when the microscope slide is placed into or removed from the base by pushing or pulling on the slide.

A biological material may also be fixed to a surface of the slide by a method comprising the steps of (a) obtaining a biological sample in an aqueous supernatant and placing a least a portion of said sample on a surface to which part of the sample is to be fixed; (b) removing aliquot volumes of said supernatant replacing the same with a similar volume of alkyl alcohol wherein said removal and replacement occurs a plurality of times so as to gradually fix the part of sample to the surface. The alkyl alcohol may be selected from the group consisting of the alkyl alcohol may be a $C_1$-$C_{12}$ alcohol, a $C_1$-$C_6$ alcohol, or methanol.

Identification and enumeration of fluorescent in situ hybridization ("FISH") signals produced with respect to nuclear components hybridized in situ with fluorescent markers may be performed by a number of different methods. One method which may find use comprises the steps of acquiring 200 with an epi-fluorescence microscope a plurality of images at different focal planes in each fluorescence channel corresponding to the hybridized FISH markers; selecting 300 a best focused image from said plurality of images for each nucleus, acquiring 400 with said epi-fluorescence microscope a plurality of images above and below the focal plane of said best focused image for each nucleus; selecting 500 for each nucleus the one focal plane above and the one focal plane below the focal plane of said best focused image in which the image is best focused; combining 600 said images from the one focal plane above and below said best focused image with said best focused image each nucleus to produce a combined image for said nucleus; and analyzing 700 the combined image for each nucleus to separate background pixels from signal pixels, and to determine areas of produced signals corresponding to a pre-set size and shape criteria corresponding to a non-artifactual target.

In an embodiment method for detecting circulating nucleated fetal cells, blood may, for example be transferred to a conical tube with volume expanded. The volume may then be mixed and added to prepared gradients. The density centrifugation gradient may be loaded manually by use of a pipettor or alternatively, it has been found, by means of a disposable plastic capillary funnel that allows unassisted loading of gradients by gravity. Tubes may then be centrifuged with centrifuge brake turned off to prevent disruption of the gradient when slowing down. The nucleated cells may be removed and may further be diluted, and then centrifuged once again. After removal of the supernatant, the cells may be resuspended, for example in PBS.

Cells may then be deposited onto a microscope slide, such as a poly-L-lysine coated slide or slide chamber, as discussed above. Methanol followed by 2% formaldehyde in PBS (=phosphate buffered saline, e.g. at ph 7.4), after pouring off of the methanol, may be used to fix the cells to the slide. The supernatant may be removed in aliquots, with introduction of methanol gradually. Such technique avoids abrupt changes in solvent properties and may gradually fix target materials. After any methanol/formaldehyde/PBS solution has been removed, the fixed cells may be stored in PBST (=PBS with 0.05% Tween 20) until ready for immunostaining.

In one immunostaining technique, the slides may be incubated with antibody, e.g., anti-mouse IgG-HRP (=peroxidase-conjugated Rabbit Anti-Mouse IgG) conjugate and/or AntiHb$_E$-CRTX (Anti-hemoglobin (epsilon chain) monoclonal antibody). Follow-up staining with a DNA complexing agent, such as DAPI (4'-6-diamidino-2-phenylindole) which forms fluorescent complexes with natural double-stranded DNA, may also be performed. Slides may be equilibrated in PBS, with a pepsin stock solution being used to improve nuclei concentration. Nuclei may be fixed onto slides using, for example, a formaldehyde, $MgCl_2$ in PBS solution followed by dehydration in an ethanol series and air drying.

Probe hybridization may then be undertaken. The probe may be thermally cycled on the slide, and the slides may then be placed into a rack as described above and then placed in bulk into a humidified FISH chamber and allowed to hybridize. Non-specifically bound probe can then be removed by methods known in the art. The probe treated sample may then be counterstained with a DNA stain, such as DAPI, dehydrated in an ethanol series and air dried. The samples on the slides may then be imaged to determine binding of the antibody and DNA stain, and from binding characteristics to determine the characteristics of the sample.

In one possible selection, the antibody may include a biotinylated tyramide functionality which in itself is not detectable. After FISH treatment, however, the antibody may be elucidated by using streptavidin labeled with a fluorophore.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims.

We claim:

1. A process within an epi-fluorescence system for identifying and enumerating fluorescent in situ hybridization ("FISH") signals produced with respect to nuclear components hybridized in situ with fluorescent markers comprising;

acquiring using an epi-fluorescence microscope a plurality of images at different focal planes in each fluorescence channel corresponding to the hybridized FISH markers;

selecting a best focused image from said plurality of images for each nucleus;

selecting for each nucleus the one focal plane above and the one focal plane below the focal plane of said best focused image in which the image is best focused;

combining said images from the one focal plane above and below said best focused image with said best focused image of each said nucleus to produce a combined image for said nucleus;

analyzing the combined image of each nucleus to separate background pixels from signal pixels, and to determine areas of produced signals corresponding to pre-set size and shape criteria corresponding to a non-artifactual target; and, outputting results of said analyzing step on a display.

* * * * *